United States Patent [19]

Cooper

[11] Patent Number: 4,778,904

[45] Date of Patent: Oct. 18, 1988

[54] INTERMEDIATES FOR MAKING 16-PHENOXY- AND 16-(SUBSTITUTED PHENOXY)-PROSTATRIENOIC ACID DERIVATIVES

[75] Inventor: Gary F. Cooper, Mountain View, Calif.

[73] Assignee: Syntex (U.S.A.) Inc., Palo Alto, Calif.

[21] Appl. No.: 2,339

[22] Filed: Jan. 9, 1987

Related U.S. Application Data

[63] Continuation of Ser. No. 774,814, Sep. 13, 1985, abandoned, which is a continuation-in-part of Ser. No. 658,950, Oct. 10, 1984, abandoned.

[51] Int. Cl.[4] .................. C07D 309/08; C07C 49/207
[52] U.S. Cl. ..................................... 549/415; 549/473; 549/214; 556/436; 568/330
[58] Field of Search ............. 549/415, 214, 473; 556/436; 568/330

[56] References Cited

U.S. PATENT DOCUMENTS

| | | | |
|---|---|---|---|
| 3,880,712 | 4/1975 | Moore | 195/51 R |
| 3,985,791 | 10/1976 | Muchowski et al. | 260/473 A |
| 4,001,300 | 1/1977 | Axen | 260/473 A |
| 4,123,463 | 10/1978 | Bundy | 260/586 R |
| 4,138,574 | 2/1979 | Magerlein | 560/53 |
| 4,158,667 | 6/1979 | Axen | 260/413 |
| 4,171,327 | 10/1979 | Bundy | 260/586 R |
| 4,178,457 | 12/1979 | Van Horn et al. | 560/53 |
| 4,235,822 | 11/1980 | Axen | 568/330 |
| 4,304,907 | 12/1981 | Nelson | 542/426 |
| 4,529,812 | 7/1985 | Collins et al. | 560/121 |
| 4,600,785 | 7/1986 | Cooper et al. | 549/212 |

FOREIGN PATENT DOCUMENTS 0146935 7/1985 European Pat. Off. .

OTHER PUBLICATIONS

M. Midland et al., J. Am. Chem. Soc., 102(2), 867-9, (1980).
C. H. Lin et al., J. Org. Chem., 47, 615-20, (1982).
T. Imamoto et al., Tet. Lett., 25(38), 4233-6, (1984).

*Primary Examiner*—Nicky Chan
*Attorney, Agent, or Firm*—Derek P. Freyberg

[57] ABSTRACT

Compounds of the formula

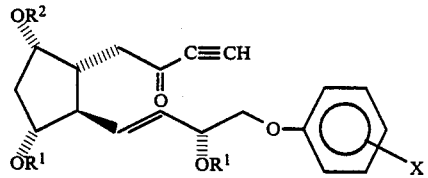

where $R^1$ and $R^2$ are hydrogen or an ether-forming group and X is hydrogen, halo, trifluoromethyl, lower alkyl, or lower alkoxy, are useful intermediates for making PGE and PGF derivatives having an allenic function.

8 Claims, No Drawings

INTERMEDIATES FOR MAKING 16-PHENOXY- AND 16-(SUBSTITUTED PHENOXY)-PROSTATRIENOIC ACID DERIVATIVES

CROSS-REFERENCE TO THE RELATED APPLICATIONS

This application is a continuation of my copending application Ser. No. 06/774,814, filed Sept. 13, 1985, abandoned, which is a continuation-in-part of my application Ser. No. 06/658,950, filed Oct. 10, 1984, now abandoned.

DESCRIPTION OF THE INVENTION

The present invention relates to a novel intermediate useful for making 16-phenoxy- and 16-(substituted phenoxy)-prostatrienoic acid derivatives. More particularly, this invention relates to the compounds of Formula I

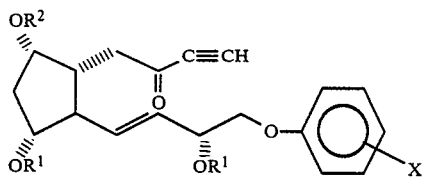

wherein $R^1$ and $R^2$ are hydrogen or an ether forming radical; and

X is hydrogen, halo, trifluoromethyl, lower alkyl or lower alkoxy.

The compounds of this invention are useful as intermediates in preparing the compounds represented by formulas II and III:

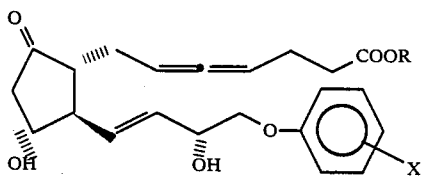

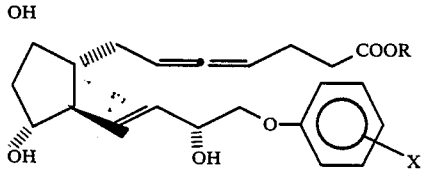

wherein R is hydrogen, lower alkyl or a pharmaceutically acceptable, non-toxic salt of a compound wherein R is hydrogen; X is hydrogen, halo, trifluoromethyl, lower alkyl or lower alkoxy.

These compounds are the subjects of U.S. Pat. Nos. 3,985,791 and 4,178,457.

The compound of formula I may be converted to a specific propargylic alcohol isomer by means of stereo-specific reagents. This propargylic alcohol may then be converted to the compounds of formula II or III by the synthetic scheme set out in U.S. Pat. No. 4,600,785.

Definitions

For the purpose of this invention, the term "lower alkyl" or "alkyl" mean a straight or branched alkyl radical of 1 to 6 carbon atoms. Examples of such radicals are methyl, ethyl, propyl, isopropyl, butyl, t-butyl, i-butyl, sec-butyl, pentyl, hexyl and the like.

"Lower alkoxy" means a RO— wherein R is lower alkyl.

"Halo" refers to fluoro, chloro, bromo, and iodo.

"Aryl" refers to phenyl, naphthyl, or the like.

"Aralkyl" refers to a benzene, naphthyl or similar aromatic moiety having a lower alkyl chain wherein lower alkyl is defined above.

"Substituted aralkyl" refers to a radical wherein the aromatic group is substituted with one or more lower alkyl, halo, or lower alkoxy radicals as these latter terms are defined above.

The compounds of this invention possess asymmetric centers and thus can be produced as racemic mixtures or as individual R,S-enantiomers. The individual enantiomers may be obtained by resolving a racemic mixture of the starting material. Alternatively, the individual R or S enantiomers may be made by starting with an individual R or S isomer. It is understood that the racemic mixture and the individual R,S-enantiomers are encompassed within the scope of this invention. The numbering which will be used for these compounds herein is as follows:

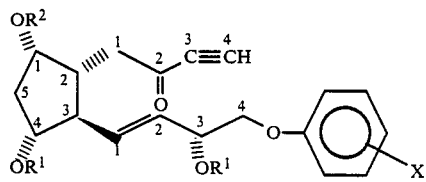

The synthesis of these compounds follows the following scheme:

REACTION SCHEME I

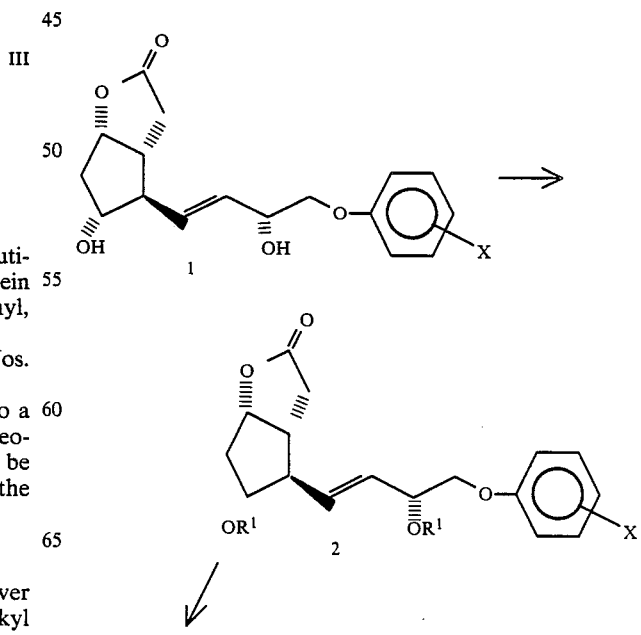

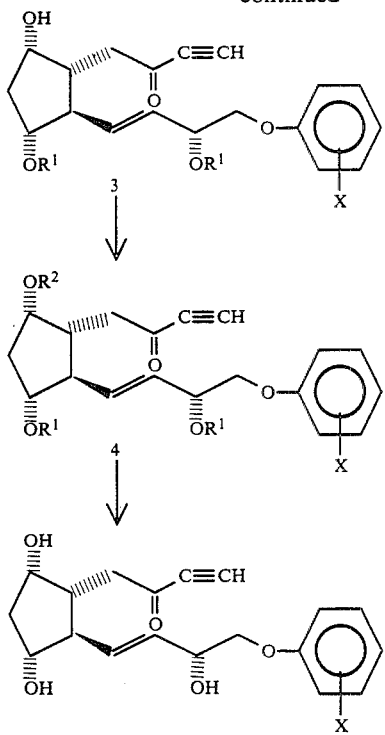

In the preceding schematics, $R^1$ and $R^2$ are ether-forming groups and X is defined hereinabove.

The starting material, formula 1, can be prepared according to the procedures set forth in U.S. Pat. Nos. 3,880,712; 3,985,791; and 4,304,907, which procedures are incorporated herein by reference and made a part hereof.

Before opening the lactone ring of formula 1, the two hydroxyl groups are converted to ethers. While any ether-forming reagent may be used, it is preferred to form ethers which are base-stabile, acid-labile in nature. Such preferred groups may be any ether-forming group which will not be hydrolyzed when treated with a strong aqueous base such as sodium or potassium hydroxide, but will be hydrolyzed by acid under mild conditions, conditions which will not result in degradation of the end product as exemplified by formulas II and III. Examples of such groups which are base-stabile, yet acid-labile are tetrahydrofuranyl, tetrahydropyranyl, 2-ethoxyethyl, and the like.

It is preferred to protect the position-4 and the butenyl side-chain hydroxyl groups with tetrahydropyranyl, tetrahydrofuranyl, or 2-ethoxyethyl. Ether formation with any of these groups is generally carried out in an aprotic solvent such as a halogenated hydrocarbon with an acid catalyst using amounts and conditions well known in the art. Most preferably, the ether forming reagent will be dihydropyran, at least about 2.1 equivalents, the reaction being carried out in methylene chloride in the presence of p-toluenesulfonic acid. The reaction is generally carried out at between about 20°–50° C., preferably at ambient temperature over a period of 15 minutes to 4 hours, preferably about 2 hours.

The ketone of formula 3 is made using lithium acetylide, the reaction being carried out in a polar solvent under an inert atmosphere, preferably at reduced temperature. The lithium acetylide is generated in situ by adding a lithium reagent such as N-butyllithium to a cooled solution of acetylene gas in the appropriate solvent. This mixture is allowed to react at reduced temperature, i.e., about −78° C., 15 to 60 min. The lactone of formula 2 is then added to the solution containing the lithium acetylide, the addition taking place at the reduced temperature. The cold bath is then removed and the reaction mixture allowed to warm to room temperature. The reaction usually is complete by the time the reaction mixture reaches room temperature. A saturated salt solution is then added, for example, ammonium chloride, with vigorous stirring. Water is then added to dissolve the precipitated salts after which the product is extracted into an appropriate organic solvent and further purified by conventional means to give the compound of formula 3, the $\alpha,\beta$-acetylenic ketone.

The compound of formula 3 then may be converted either to the trihydroxy compound or treated with an ether forming group to protect the position 1-hydroxyl group. If the compound of formula 3 is to be protected so that further synthetic work can be done with the compound, the hydroxyl group may be converted to any ether. However, it is preferable to convert the position 1-hydroxyl group to a base labile, ether-forming substituent. Such a group is best exemplified by —$SiR_4R_5R_6$ wherein $R_4$, $R_5$, and $R_6$ are alkyl, phenyl, or arylalkyl, except that all three may not be methyl simultaneously. Particularly preferred silyl groups are t-butyldimethylsilyl, triisopropylsilyl, triphenylsilyl, t-butyldiphenylsilyl, and (2,4,6-tri-t-butylphenoxy)dimethylsilyl radicals.

When a silylating agent is employed, standard conditions normally used for such a reagent will be used. For example, the reaction is generally carried out in a polar aprotic solvent with an excess of silylating agent, i.e., 2.2 to 4 equivalents, and an excess relative to the silylating agent of some nitrogen-containing compound, such as imidazole, pyridine, a derivative of either, diisopropylethyl amine, or the like.

For etherification of the compounds herein, the preferred nitrogen-containing bases are sterically hindered ones such as 2,6-lutidine and 2,4,6-collidine. About 3 equivalents of t-butyldimethylsilylylchloride are normally employed. The reaction is carried out in dry dimethylformamide. The reaction is carried out at about ambient temperature and is usually completed in 16 to 20 hours.

The compounds of formula I wherein $R^1$ and $R^2$ are hydrogen are obtained by hydrolysis of the $R^1$ and $R^2$ ether-forming groups. This may be carried out by acid or base depending upon the lability of those respective blocking groups. If the blocking groups are all acid labile, then an alkanoic acid of 1–6 carbon atoms or a hydrogen halide may be used to effect the hydrolysis. Where an R group is base labile, a dilute solution of a strong base, such as one of the alkaline metal hydroxide bases, i.e., lithium hydroxide, sodium hydroxide, potassium hydroxide, or the like, may be used.

When the hydrolyzing agent is an alkanoic acid, acetic acid is the preferred reagent. Acetic acid hydrolysis of ether-forming groups, particularly tetrahydrofuranyl, tetrahydropyranyl, or a trialkylsilyl group, or the like, is well known in the art. For example, the standard hydrolysis procedure uses acetic acid and a polar solvent, such as tetrahydrofuran, or the like. The ether, glacial acetic acid, water and organic solvent are mixed in a flask under nitrogen and heated at low temperature, between about 20°–60° C., preferably 40° C., for up to 16 hours, preferably 12 hours. Alternatively, hydrolysis of the acid labile ether groups may be effected by hydrogen halide, preferably an aqueous solution of the acid dispersed in a water immiscible solvent, preferably with a scavenging agent to react with the released blocking group. The reaction is effected at a temperature between about −40° to 40° C. over a period of about 5 minutes to 4 hours. This method comprises stirring an aqueous solution of hydrogen halide with a water immiscible solvent in which the intermediate has been dissolved. The hydrogen halide may be hydrogen fluoride, hydrogen chloride, hydrogen bromide, or hydrogen iodide. The acid should be present in a slight molar excess, for example, about at least 2.025 equivalents of acid, though the reaction can be effected using a large excess of acid, i.e., up to 10 equivalents or more. Preferably 2.05 to 3.0 equivalents will be used, most preferably about 2.5 equivalents. Any water immiscible organic solvent may be used, but it is preferred to use a halogenated hydrocarbon such as, for example, methylene chloride, dichloroethane, and the like. To trap the released blocking group, a reactive scavenging material is added to the reaction mixture. This scavenging material is preferably a mercaptan, for example, mercaptoethanol. The scavenging material should be present in an amount of 2.0 to 3.0 equivalents, preferably about 2.0 equivalents. The reaction is completed in about 30–60 minutes at a temperature between about −30° to 50° C., preferably at about room temperature.

When the ether is to be hydrolyzed by base, a dilute solution of a strong base such as one of the alkali metal hydroxide bases will be used. For the purpose of this work, a dilute solution is one which has a concentration of 0.05 to 2M, preferably about 0.5M. An appropriate solvent is, for example, 2-methoxyethanol or a similar polar solvent which is miscible with water. Preferably, an inert atmosphere is maintained. In terms of temperature and time, the reaction is effected by heating the solvent to reflux for up to about 72 hours.

The method for the stereospecific production of the propargyl alcohol is schematically depicted in Reaction Scheme II.

REACTION SCHEME II

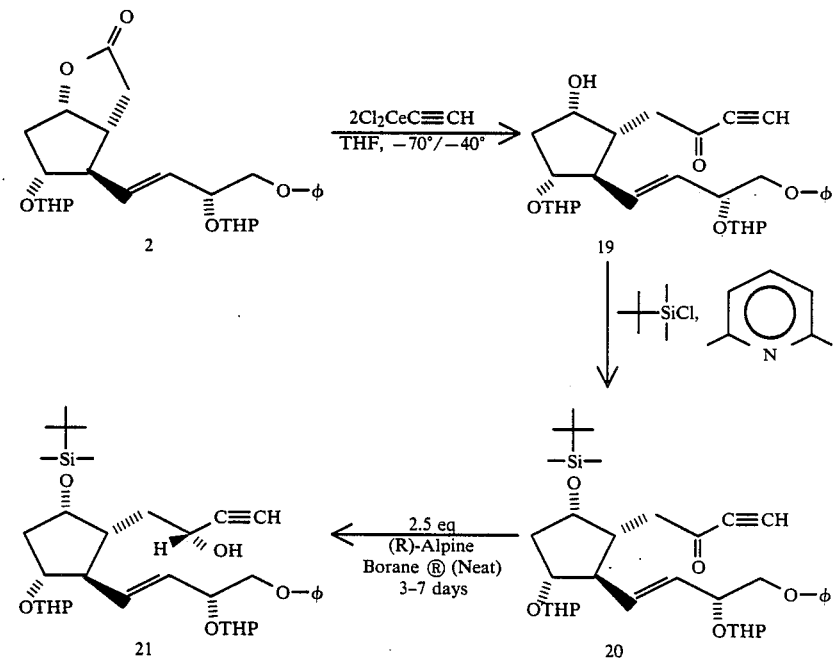

The lactone ring of 2 is simultaneously cleaved and the acetylenic group added by reaction of the lactone with a 1 to 3 molar excess of dichlorocerium acetylide 18. Compound 18 is prepared by reacting CeCl$_3$ (anhydrous) with LiC≡CH in THF at −75° C. After 30 minutes the lactone solution, dissolved in, for example, THF, is added. The temperature should be kept in the range of between about −75° and −30°, and is preferably about −40°. The mixture is added to aqueous NH$_4$Cl. The organic layer is washed with NH$_4$Cl and water. The mixture is dried, filtered and the solvent removed, allowing the isolation of the ethynyl ketone 19.

The unprotected alcohol 19 is protected with t-butyldimethylchlorosilane by reacting it in the presence of a sterically hindered nitrogen containing base, such as lutidine. Any alcohol protecting group can be used but it is preferred that t-butyldimethylsilyl be used as protecting group for this hydroxyl. This results in a molecule that has two different types of alcohol protecting groups, allowing each to be reacted differently.

The ethynyl ketone 20 is then reduced. There are two types of reductions that can be done at this point, stereospecific or non-stereospecific. The non-stereospecific reduction is accomplished by standard hydride reducing agents, for example, lithium aluminum hydride, sodium borohydride and the like (see H. O. House, *Modern Synthetic Reactions,* Benjamin, 1972, Chapter 2). The stereospecific reduction is accomplished using an optically active reducing agent, for example, LiAlH$_4$/[(2S,3R)-(+)-4-dimethylamino-1,2-diphenyl-3-methyl-2-butanol], sometimes referred to as LiAlH$_4$-/Darvon ® alcohol, or, alternatively, (R)-Alpine Borane ® (B-isopinocampheyl-9-borabicyclo[3.3.1]nonane). The preferred reducing agent is (R)-Alpine Borane ® (see M. M. Midland et al, *J. Am. Chem. Soc.,* 102, 867

(1980). The ketone and the Alpine Borane ® are mixed neat and stirred for several days. It is preferred to have an excess of the borane to speed the reaction. The preferred ratio is about 1:2.3.

Once a compound of Formula 21 has been obtained, whether by stereospecific reaction or not, the rest of the reaction sequence of Reaction Scheme I can be carried out.

The propargylic alcohol, Formula 21, is dissolved in the trialkyl orthoacetate, preferably under nitrogen, along with a catalytic amount of alkanoic acid, usually about a 1% volume relative to the orthoacetate. The orthoester reacts with the propargyl alcohol, Formula 21, to give a mixed trialkylorthoester which is not isolated but caused to rearrange in situ by heating the pot. The reaction flask is immersed in a preheated oil bath, for example one at about 150°–250° C., and stirred for a short period, about 30 minutes while maintaining the pot temperature between about 100°–130° C., preferably between about 110°–120° C. During the heating period, a mixture of orthoacetate and alkanoic acid, in the same ratio noted above, is added to the system while concurrently distilling out of the reaction system an equivalent volume of trialkyl orthoester-alkanol-acid. The reaction bath is preferably maintained at a temperature between about 170°–175° C. during the distillation process. To further illustrate and exemplify the practice of this invention, the following non-limiting examples are provided.

EXAMPLE 1

(1α-Hydroxy-4α-(tetrahydropyran-2-yloxy)-3β-(3α-(tetrahydropyran-2-yloxy)-4-phenoxy-1(E)-buten-1-yl)cyclopent-2α-yl)acetic acid lactone A 1 liter round bottom flask equipped with a magnetic stirring bar and Drierite ® drying tube was charged with 16.5 g of (1α,4α-dihydroxy-3β-(3α-hydroxy-4-phenoxy-1(E)-buten-1-yl)-cyclopent-2α-yl)acetic acid lactone, 500 ml of methylene chloride, 8.8 ml of dihydropyran and a few crystals of p-toluenesulfonic acid.H₂O. This mixture was stirred at room temperature for 2 hours. Two drops of triethylamine were added and the solution stirred for 2 minutes. The reaction mixture was washed with 1×50 ml of saturated aqueous sodium chloride and dried over sodium sulfate. Evaporation of the solvent gave a residue which was taken up in a minimum amount of ethyl acetate and charged onto a 7.5 cm diameter column filled with 500 g of silica gel packed in hexane. The column was then eluted with a gradient of 20% to 40% ethyl acetate in hexane. Appropriate fractions were combined and stripped to dryness to afford the title compound.

Proceeding in a similar manner, but substituting for the starting compound in the preceding paragraph the appropriately substituted phenoxy lactone, the following compounds may be prepared:

(1α-hydroxy-4α-(tetrahydropyran-2-yloxy)-3β-(3α-(tetrahydropyran-2-yloxy)-4-(m-trifluoromethylphenoxy)-1(E)-buten-1-yl)cyclopent-2α-yl)acetic acid lactone;

(1α-hydroxy-4α-(tetrahydropyran-2-yloxy)-3β-(3α-(tetrahydropyran-2-yloxy)-4-(m-fluorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-fluorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(p-fluorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(p-chlorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-chlorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(m-chlorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(m-bromophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-bromophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(p-bromophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(m-methylphenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-methylphenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(p-methylphenoxy)-1(E)-buten--yl)-cyclopent-2α-yl)acetic acid lactone;

(1α-hydroxy-4α-(tetrahydropyran-2-yloxy)-3β-(3α-(tetrahydropyran-2-yloxy)-4-(m-methoxyphenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-methoxyphenoxy)-1(E)-buten-1-yl)-cyclopent-2α-yl)acetic acid lactone; and (1α-hydroxy-4α-(tetrahydropyran-2-yloxy)-3β-(3α-(tetrahydropyran-2-yloxy)-4-(p-methoxyphenoxy)-1(E)-buten-1-yl)-cyclopent-2α-yl)acetic acid lactone.

EXAMPLE 2

(1α-Hydroxy-4α-(tetrahydropyran-2-yloxy)-3β-(3α-(tetrahydropyran-2-yloxy)-4-phenoxy-1-(E)-buten-1-yl)-cyclopent-2α-yl)-1-but-3-yn-2-one A 100 ml 2-neck round bottom flask equipped with magnetic stirrer and septum caps with a nitrogen/vacuum inlet was charged with 7 ml of dry tetrahydrofuran. The flask and solvent was cooled to −78° C. with a dry ice/isopropanol bath, and vacuum purged with nitrogen five times. Over 3 minutes there was injected from a gas-tight syringe below the surface of the cold tetrahydrofuran 84 ml of purified acetylene gas. This acetylene gas had been purified by passage through a dry ice cooled trap, 3 concentrated sulfuric acid bubblers and a Drierite ® tower. Over 9 minutes there was then added dropwise 1.56 ml of 2.05 molar n-butyllithium/hexane. This mixture was stirred for 14 minutes at −78° C. The protected lactone (1.25 g) from the preceding example was dissolved in 5 ml of dry tetrahydrofuran and added to the lithium acetylide solution over 5 minutes. The addition flask was washed with 1 ml of dry tetrahydrofuran. After 10 minutes at about −78° C., the cold bath was removed and the reaction apparatus allowed to warm to room temperature. The solution changed from colorless to bright orange over about 22 minutes during this warming process. Ten ml of saturated aqueous ammonium chloride was then added and the solution stirred vigorously for 10 minutes. Enough water was then added to dissolve the precipitated salts, followed by 15 ml of diethyl ether. The aqueous layer was extracted 1×10 ml of ether. The combined organic layers were washed with 2×10 ml of water, 1×10 ml brine and the organic layer dried over magnesium sulfate. This dried organic extract was filtered and concentrated in vacuo to give the title compound as a crude product.

The crude product was further purified by percolation through 13 g of silica gel packed in 40% ether/hexane. The product was eluted with 500 ml of the same solvent followed by 200 ml of 50% ether/hexane while collecting 20 ml fractions. Fractions 6–20 were combined and concentrated in vacuo to give a colorless, very viscous oil.

EXAMPLE 3

(1α-t-butyldimethylsilyloxy-4α-(tetrahydropyran-2-yloxy)-3β-(3α-(tetrahydropyran-2-yloxy)-4-phenoxy-1-(E)-buten-1-yl)-cyclopent-2α-yl)-1-but-3-yn-2-one In a 2 ml glass vial equipped with magnetic stirrer and septum cap was dissolved 93 milligrams of the α,β-acetylenic ketone in 1 ml of dry dimethylformamide. To this was added 86 mg of t-butyldimethylchlorosilane with stirring until the reactants were dissolved. There was then added 82 microliters of neat 2,6-lutidine. This solution was stirred overnight at room temperature. Water (1 ml) was then added and the solution stirred vigorously for 10 minutes. The stirred solution was then transferred to a separatory funnel, the reaction flask being washed with water and ether. The aqueous layer was extracted 2×1 ml of ether. The combined organic layers were extracted with 1×2 ml of water, 1×2 ml 1M HCl, 1×2 ml of water, 1×2 ml of saturated aqueous sodium bicarbonate, 1×2 ml of water, 1×2 ml brine and dried over sodium sulfate powder. The dried diethyl ether solution was filtered and concentrated under vacuum to give the title compound as an orange oil.

The oil was further purified by percolating it through 1.2 g of silica gel packed in 5% ethyl acetate/hexane. The product was eluted with 20 ml of 5% ethyl acetate/hexane followed by 30 ml of 10% ethyl acetate/hexane while collecting 4 ml fractions. Fractions 4–13 were collected, combined and concentrated in vacuo to give the pure product as a colorless oil.

EXAMPLE 4

(1α,4α-dihydroxy-3β-(3α-hydroxy)-4-phenoxy-1-(E)-buten-1-yl)-cyclopent-2α-yl)-1-but-3-yn-2-one A 3 milligram aliquot of the α,β-acetylenic ketone of Example 2 was dissolved in a solution of glacial acetic acid (10 ml), water (6 ml) and tetrahydrofuran (1.7 ml). This reaction mixture was stirred for 12 hours at 40° C. under nitrogen. Solvents were removed under reduced pressure. The resulting residue was subjected to azeotropic distillation with toluene (3×10 ml). Further purification was effected on a silica gel column made up in hexane, the product being eluted with 75% ethyl acetate in hexane. Appropriate fractions were combined and evaporated to dryness under reduced pressure to give the title compound. Proceeding in a similar manner, ketones prepared in the manner of Example 2 are converted to their corresponding hydroxy analogs, e.g.

(1α,4α-dihydroxy-3β-(3α-hydroxy)-4-(m-trifluoromethylphenoxy)-1(E)-buten-1-yl)cyclopent-2α-yl)-1-but-3-yn-2-one;

(1α,4α-dihydroxy-3β-(3α-hydroxy)-4-(m-fluorophenoxy)-1(E)-buten-1-yl)-cyclopent-2α-yl)-1-but-3-yn-2-one;

(1α,4α-dihydroxy-3β-(3α-hydroxy)-4-(o-fluorophenoxy)-1(E)-buten-1-yl)-cyclopent-2α-yl)-1-but-3-yn-2-one;

(1α,4α-dihydroxy-3β-(3α-dihydroxy)-4-(p-fluorophenoxy)-1(E)-buten-1-yl)-cyclopent-2α-yl)-1-but-3-yn-2-one;

(1α,4α-dihydroxy-3β-(3α-hydroxy)-4-(p-chlorophenoxy)-1(E)-buten-1-yl)-cyclopent-2α-yl)-1-but-3-yn-2-one;

(1α,4α-dihydroxy-3β-(3α-hydroxy)-4-(o-chlorophenoxy)-1(E)-buten-1-yl)-cyclopent-2α-yl)-1-but-3-yn-2-one;

(1α,4α-dihydroxy-3β-(3α-hydroxy)-4-(m-chlorophenoxy)-1(E)-buten-1-yl)-cyclopent-2α-yl)-1-but-3-yn-2-one;

(1α,4α-dihydroxy-3β-(3α-hydroxy)-4-(m-bromophenoxy)-1(E)-buten-1-yl)-cyclopent-2α-yl)-1-but-3-yn-2-one;

(1α,4α-dihydroxy-3β-(3α-hydroxy)-4-(o-bromophenoxy)-1(E)-buten-1-yl)-cyclopent-2α-yl)-1-but-3-yn-2-one;

(1α,4α-dihydroxy-3β-(3α-hydroxy)-4-(p-bromophenoxy)-1(E)-buten-1-yl)-cyclopent-2α-yl)-1-but-3-yn-2-one;

(1α,4α-dihydroxy-3β-(3α-hydroxy)-4-(m-methylphenoxy)-1(E)-buten-1-yl)-cyclopent-2α-yl)-1-but-3-yn-2-one;

(1α,4α-dihydroxy-3β-(3α-hydroxy)-4-(o-methylphenoxy)-1(E)-buten-1-yl)-cyclopent-2α-yl)-1-but-3-yn-2-one;

(1α,4α-dihydroxy-3β-(3α-hydroxy)-4-(p-methylphenoxy)-1(E)-buten-1-yl)-cyclopent-2α-yl)-1-but-3-yn-2-one;

(1α,4α-dihydroxy-3β-(3α-hydroxy)-4-(m-methoxyphenoxy)-1(E)-buten-1-yl)-cyclopent-2α-yl)-1-but-3-yn-2-one;

(1α,4α-dihydroxy-3β-(3α-hydroxy)-4-(o-methoxyphenoxy)-1(E)-buten-1-yl)-cyclopent-2α-yl)-1-but-3-yn-2-one; and (1α,4α-dihydroxy-3β-(3α-hydroxy)-4-(p-methoxyphenoxy)-1(E)-buten-1-yl)-cyclopent-2α-yl)-1-but-3-yn-2-one.

EXAMPLE 5

(1α-hydroxy-4-α-(tetrahydropyran-2-yloxy)-3β-(3α-(tetrahydropyran-2yloxy)-4-phenoxy-1(E)-buten-1-yl)-cyclopent-2α-yl)-1-but-3-yn-2-one 34.37 g of CeCl$_3$.7H$_2$O was dried at 140° for two hours in vacuo and then cooled. When cooled, the dry CeCl$_3$ was brought to atmospheric pressure with nitrogen. The CeCl$_3$ was stirred in Flask A in 300 ml dry THF. The temperature of Flask A was lowered to −75° C. in a dry ice/isopropanol bath.

In another flask (Flask B) 2160 ml of purified acetylene was added to 200 ml of dry THF at −75° C. in 250 ml shots. 52.9 ml of 1.6 m-butyllithium was then added dropwise. The resulting LiC≡CH solution was transferred rapidly to flask A by flexible needle cannulation.

20.0 g of (1α-hydroxy-4-α-(tetrahydropyran-2-yloxy)-3β-(3α-(tetrahydropyran-2-yloxy)-4-phenoxy-1(E)-buten-1-yl)-cyclopent-2α-yl)-acetic acid lactone in 90 ml of dry THF was then added to flask A. The temperature of flask A was then raised to −40° C. After 2.5 hours the solution in flask A was worked up.

The solution of flask A was added to a 1.5 l stirred solution of aqueous NH4Cl. The organic layer was separated, washed, and filtered through 45 g of Celite. After drying and removal of solvent the title compound was isolated.

Proceeding in a similar manner, but substituting for the starting compound in the preceding paragraph the appropriately substituted phenoxylactone, the following compounds may be prepared:

(1α-hydroxy-4α-(tetrahydropyran-2-yloxy)-3β-(3α-(tetrahydropyran-2-yloxy)-4-(m-trifluoromethyl-phenoxy)-1(E)-buten-1-yl)cyclopent-2α-yl)-1-but-3-yn-2-one;

(1α-hydroxy-4α-(tetrahydropyran-2-yloxy)-3β-(3α-(tetrahydropyran-2-yloxy)-4-(m-fluorophenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(o-fluorophenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(p-fluorophenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(p-chlorophenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(o-chlorophenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(m-chlorophenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(m-bromophenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(o-bromophenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(p-bromophenoxy)-1(E)-buten-1-yl)-cyclopent-2α-yl)-1-but-3-yn-2-oneo;

(1α-hydroxy-4α-(tetrahydropyran-2-yloxy)-3β-(3α-(tetrahydropyran-2-yloxy)-4-(m-methylphenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(o-methylphenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(p-methylphenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(m-methoxyphenoxy)-1(E)-buten-1-yl)-cyclopent-2α-yl)-1-but-3-yn-2-one;

(1α-hydroxy-4α-(tetrahydropyran-2-yloxy)-3β-(3α-(tetrahydropyran-2-yloxy)-4-(o-methoxyphenoxy)-1(E)-buten-1-yl)-cyclopent-2α-yl)-1-but-3-yn-2-one; and (1α-hydroxy-4α-(tetrahydropyran-2-yloxy)-3β-(3α-(tetrahydropyran-2-yloxy)-4-(p-methoxyphenoxy)-1(E)-buten-1-yl)-cyclopent-2α-yl)-1-but-3-yn-2-one.

EXAMPLE 6

(1α-t-butyldimethylsiloxy-4-α-(tetrahydropyran-2-yloxy)-3β-(3α-(tetrahydropyran-2yloxy)-4-phenoxy-1(E)-buten-1-yl)-cyclopent-2α-yl)-1-but-3-yn-2-one 19.08 g of (1α-hydroxy-4-α-(tetrahydropyran-2-yloxy)-3β-(3α-(tetrahydropyran-2yloxy)-4-phenoxy-1(E)-buten-1-yl)-cyclopent-2α-yl)-1-but-3-yn-2-one was dissolved in 115 ml of dry DMF. 11.53 g of t-butyldimethylsilyl chloride in 40 ml dry DMF was added, followed by 11.14 ml of lutidine. The reaction mixture was then stirred at room temperature for two hours, and worked up by cooling to 0° C., adding ice water, separating the organic phase, and washing with 360 ml of ethyl ether. The organic layer was dried and the solvent removed and the title compound isolated.

Proceeding in a similar manner, but substituting for the starting compound in the preceding paragraph the appropriately substituted phenoxylactone, the following compounds may be prepared:

(1α-t-butyldimethylsiloxy-4α-(tetrahydropyran-2-yloxy)-3β-(3α-(tetrahydropyran-2-yloxy)-4-(m-trifluoromethyl)-phenoxy)-1(E)-buten-1-yl)cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(m-fluorophenoxy)-1(E)-buten-1-yl)-cyclopent-2α-yl)-1-but-3yn-2-one;

(1α-t-butyldimethylsiloxy-4α-(tetrahydropyran-2-yloxy)-3β-(3α-(tetrahydropyran-2-yloxy)-4-(o-fluorophenoxy)-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(p-fluorophenoxy)-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(p-chlorophenoxy)-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(o-chlorophenoxy)-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(m-chlorophenoxy)-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(m-bromophenoxy)-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(o-bromophenoxy)-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(p-bromophenoxy)-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(m-methylphenoxy)-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(o-methylphenoxy)-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(p-methyl-phenoxy)-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(m-methoxyphenoxy-1(E)-buten-1-yl)-cyclopent-2α-yl)-1-but-3-yn-2-one;

(1α-t-butyldimethylsiloxy-4α-(tetrahydropyran-2-yloxy)-3β-(3α-(tetrahydropyran-2-yloxy)-4-(o-methoxyphenoxy)-1(E)-buten-1-yl)-cyclopent-2α-yl)-1-but-3-yn-2-one;

and (1α-t-butyldimethylsiloxy-4α-(tetrahydropyran-2-yloxy)-3β-(3α-(tetrahydropyran-2-yloxy)-4-(p-methoxyphenoxy)-1(E)-buten-1-yl)-cyclopent-2α-yl)-1-but-3-yn-2-one.

EXAMPLE 7

(1α-t-butyldimethylsiloxy-4-α-(tetrahydropyran-2-yloxy)-3β-(3α-(tetrahydropyran-2yloxy)-4-phenoxy-1(E)-buten-1-yl)-cyclopent-2α-yl)-1-but-3-yn-(R)2-ol 162.3 ml of 0.5M (R)-Alpine Borane ® was added to 19.89 g of (1α-t-butyldimethylsiloxy-4-α-(tetrahydropyran-2-yloxy)-3β-(3α-(tetrahydropyran-2yl-oxy)-4-phenoxy-1(E)-buten-1-yl)-cyclopent-2α-yl)-1-but-3-yn-2-one, the solvent removed under vacuum, and the two reactants stirred together at room temperature, under nitrogen, for five days. The reaction mixture was then diluted with 20 ml of ethyl ether, cooled with an ice bath, and 6.3 ml of freshly distilled acetaldehyde added. The reaction mixture was then allowed to warm to room temperature over 30 minutes. The volatiles were removed at 40° C. The mixture was then cooled, 105 ml of ethyl ether added, 5.37 ml of ethanolamine added dropwise and the resulting precipitate stirred for 1 hour. The mixture was filtered through a "C" sintered glass filter and the filter cake washed with 50 ml ice cold ethyl ether portions. The yellow filtrate was concentrated, dried and the solvent removed yielding the title compound. Chromatographic purification was on silica gel, elution with a gradient of 5% to 20% ethyl acetate in hexanes giving a pure colorless oil.

Proceeding in a similar manner, but substituting for the starting compound in the preceding paragraph the appropriately substituted phenoxylactone, the following compounds may be prepared:

(1α-t-butyldimethylsiloxy-4α-(tetrahydropyran-2-yloxy)-3β-(3α-(tetrahydropyran-2-yloxy)-4-(m-trifluoromethyl-phenoxy)-1(E)-buten-1-yl)cyclopent-2α-yl)-1-but-3-yn-(R)2-ol;

(1α-t-butyldimethylsiloxy-4α-(tetrahydropyran-2-yloxy)-3β-(3α-(tetrahydropyran-2-yloxy)-4-(m-fluorophenoxy)-1(E)-buten-1-yl)-cyclopent-2α-yl)-1-but-3-yn-(R)2-ol;

(1α-t-butyldimethylsiloxy-4α-(tetrahydropyran-2-yloxy)-3β-(3α-(tetrahydropyran-2-yloxy)-4-(o-fluorophenoxy)-1(E)-buten-1-yl)-cylopent-2α-yl)-1-but-3-yn-(R)2-ol;

(1α-t-butyldimethylsiloxy-4α-(tetrahydropyran-2-yloxy)-3β-(3α-(tetrahydropyran-2-yloxy)-4-(p-fluorophenoxy)-b 1(E)-buten-1-yl)-cyclopent-2α-yl)-1-but-3-yn-(R)2-ol;

(1α-t-butyldimethylsiloxy-4α-(tetrahydropyran-2-yloxy)-3β-(3α-(tetrahydropyran-2-yloxy)-4-(p-chlorophenoxy)-1(E)-buten-1-yl)-cyclopent-2α-yl)-1-but-3-yn-(R)2-ol;

(1α-t-butyldimethylsiloxy-4α-(tetrahydropyran-2-yloxy)-3β-(3α-(tetrahydropyran-2-yloxy)-4-(o-chlorophenoxy)-1(E)-buten-1-yl)-cyclopent-2α-yl)-1-but-3-yn-(R)2-ol;

(1α-t-butyldimethylsiloxy-4α-(tetrahydropyran-2-yloxy)-3β(3α-(tetrahydropyran-2-yloxy)-4-(m-chlorophenoxy)-1(E)-buten-1-yl)-cyclopent-2α-yl)-1-but-3-yn-(R)2-ol;

(1α-t-butyldimethysiloxy-4α-(tetrahydropyran-2-yloxy)-3β-(3α-(tetrahydropyran-2-yloxy)-4-(m-bromophenoxy)-1(E)-buten-1-yl)-cyclopent-2α-yl)-1-but-3-yn-(R)2-ol;

(1α-t-butyldimethylsiloxy)-4α-(tetrahydropyran-2-yloxy)-3β-(3α-(tetrahydropyran-2-yloxy)-4-(o-bromophenoxy)-1(E)-buten-1-yl)-cyclopent-2α-yl)-1-but-3-yn-(R)2-ol;

(1α-t-butyldimethylsiloxy-4α-(tetrahydropyran-2-yloxy)-3β-(3α-(tetrahydropyran-2-yloxy)-4-(p-bromophenoxy)-1(E)-buten-1-yl)-cyclopent-2α-yl)-1-but-3-yn-(R)2-ol;

(1α-t-butyldimethylsiloxy-4α-(tetrahydropyran-2-yloxy)-3β-(3α-(tetrahydropyran-2-yloxy)-4-(m-methylphenoxy)-1(E)-buten-1-yl)-cyclopent-2α-yl)-1-but-3-yn-(R)2-ol;

(1α-t-butyldimethylsiloxy-4α-(tetrahydropyran-2-yloxy)-3β-(3α-(tetrahydropyran-2-yloxy)-4-(o-methylphenoxy)-1(E)-buten-1-yl)-cyclopent-2α-yl)-1-but-3-yn-(R)2-ol;

(1α-t-butyldimethylsiloxy-4α-(tetrahydropyran-2-yloxy)-3β-(3α-(tetrahydropyran-2-yloxy)-4-(p-methylphenoxy)-1(E)-buten-1-yl)-cyclopent-2α-yl)-1-but-3-yn-(R)2-ol;

(1α-t-butyldimethylsiloxy-4α-(tetrahydropyran-2-yloxy)-3β-(3α-(tetrahydropyran-2-yloxy)-4-(m-methoxyphenoxy)-1(E)-buten-1-yl)-cyclopent-2α-yl)-1-but-3-yn-(R)2-ol;

(1α-t-butyldimethylsiloxy-4α-(tetrahydropyran-2-yloxy)-3β-(3α-(tetrahydropyran-2-yloxy)-4-(o-methoxyphenoxy)-1(E)-buten-1-yl)-cyclopent-2α-yl)-1-but-3-yn-(R)2-ol;

and (1α-t-butyldimethylsiloxy-4α-(tetrahydropyran-2-yloxy)-3β-(3α-(tetrahydropyran-2-yloxy)-4-(p-methoxyphenoxy)-1(E)-buten-1-yl)-cyclopent-2α-yl)-1-but-3-yn-(R)2-ol.

What is claimed is:

1. A compound of the formula

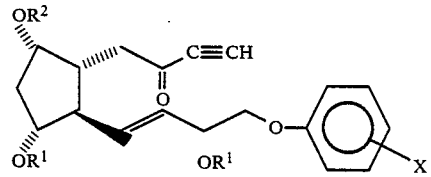

in which $R^1$ is hydrogen or a base-stabile, acid-labile ether-forming group;

$R^2$ is hydrogen or a base-labile ether-forming group; and

X is hydrogen, halo, trifluoromethyl, lower alkyl or lower alkoxy.

2. The compound of claim 1 wherein X is hydrogen.

3. The compound of claim 2 wherein $R^2$ is hydrogen.

4. The compound of claim 3 wherein $R^1$ is hydrogen, namely [1α,4α-dihydroxy-3β-(3α-hydroxy-4-phenoxy-1-(E)-buten-1-yl)cyclopent-2α-yl]-1-but-3-yn-2-one.

5. The compound of claim 3 wherein $R^1$ is tetrahydropyranyl, tetrahydrofuranyl, or 2-ethoxyethyl.

6. The compound of claim 5 wherein $R^1$ is tetrahydropyranyl, namely [1α-hydroxy-4α-(tetrahydropyran-2-yloxy)-3β-(3α-(tetrahydropyran-2-yloxy)-4-phenoxy-1-(E)-buten-1-yl)cyclopent-2α-yl]-1-but-3-yn-2-one.

7. The compound of claim 2 wherein $R^1$ is a base-stabile, acid-labile ether-forming group and $R^2$ is t-butyldimethylsilyl, triisopropylsilyl, triphenylsilyl, t-butyldiphenylsilyl, or (2,4,6-tri-t-butylphenoxy)dimethylsilyl.

8. The compound of claim 7 wherein $R^1$ is tetrahydropyranyl and $R^2$ is t-butyldimethylsilyl, namely [1α-(t-butyldimethylsilyloxy)-4α-(tetrahydropyran-2-yloxy)-3β-(3α-(tetrahydropyran-2-yloxy)-4-phenoxy-1-(E)-buten-1-yl)cyclopent-2α-yl]-1-but-3-yn-2-one.

* * * * *